United States Patent [19]

Peet et al.

[11] Patent Number: 4,871,732
[45] Date of Patent: Oct. 3, 1989

[54] SUBSTITUTED IMIDAZO(2,1-B)QUINAZOLIN-5(3H)-ONES AND RELATED TRICYCLIC COMPOUNDS AND USE AS BRONCHODILATORS

[75] Inventors: Norton P. Peet, Cincinnati, Ohio; Shyam Sunder, Indianapolis, Ind.

[73] Assignee: Merrell Dow Pharmaceuticals Inc., Cincinnati, Ohio

[21] Appl. No.: 247,797

[22] Filed: Sep. 22, 1988

[51] Int. Cl.[4] ............... A61K 31/505; A61K 31/535; C07D 471/14; C07D 487/04
[52] U.S. Cl. .............................. 514/212; 514/233.2; 514/254; 514/267; 540/600; 544/115; 544/250; 544/251
[58] Field of Search ............... 540/600; 544/115, 250, 544/251; 514/212, 233.2, 254, 267

[56] References Cited

U.S. PATENT DOCUMENTS 3,875,161  4/1975  Hardtmann ................ 544/251
4,725,596  2/1988  Friary ....................... 514/214

*Primary Examiner*—Robert W. Ramsuer
*Attorney, Agent, or Firm*—John J. Kolano

[57] ABSTRACT

The present invention is directed to a group of compounds which are imidazo[2,1-b]quinazolin-5(3H)-ones, related tricyclic compounds, and pharmaceutically acceptable salts thereof. These compounds are useful as bronchodilators. These compounds are prepared by the reaction of an appropriate hydrazine with an appropriate 1-substituted-2-methyl-2-imidazoline or chemically equivalent compound.

14 Claims, No Drawings

SUBSTITUTED IMIDAZO(2,1-B)QUINAZOLIN-5(3H)-ONES AND RELATED TRICYCLIC COMPOUNDS AND USE AS BRONCHODILATORS

The present invention is directed to a group of compounds which are substituted imidazo[2,1-b]quinazolin-5(3H)-ones and related tricyclic compounds. These compounds have the following general formula:

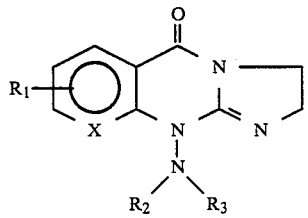

wherein
$R_1$ is H, halogen, or $CH_3$;
$NR_2R_3$ is a di(lower alkyl) amino, 1-pyrrolidinyl, 1-piperidinyl, 1-homopiperidinyl, 4-methyl-1-piperizinyl, or 4-morpholinyl; and
X is —CH= or —N=.

The halogen referred to above is Fl, Cl, or Br. The lower alkyl groups referred to above contain 1 to 4 carbon atoms and can be exemplified by groups such as methyl, ethyl, propyl, isopropyl, butyl, and isobutyl.

The acid addition salts of the above compounds with pharmaceutically acceptable acids are considered equivalent to the above amines for purposes of this invention. Illustrations of the above are the salts with (a) inorganic acids such as, for example, hydrochloric, hydrobromic, sulfuric, phosphoric, and like acids; (b) with organic carboxylic acids such as, for example, acetic, propionic, glycolic, lactic, pyruvic, malonic, succinic, fumaric, malic, tartaric, citric, ascorbic, maleic, hydroxymaleic and dihydroxymaleic, benzoic, phenylacetic, 4-aminobenzoic, 4-hydroxybenzoic, anthranilic, cinnamic, salicylic, 4-aminosalicylic, 2-phenoxybenzoic, 2-acetoxybenzoic, mandelic, and like acids; and (c) with organic sulfonic acids such as, for example, methanesulfonic acid and p-toluenesulfonic acid.

The imidazo[2,1-b]quinazolin-5(3H)-ones, related tricyclic compounds, and pharmaceutically acceptable salts described herein, are bronchodilators. Thus, they are useful in the treatment of bronchial disorders such as bronchial asthma. The present invention is further directed to a method of effecting bronchodilation.

In practicing the method of this invention, a pharmaceutically effective amount of one or more imidazo[2,1-b]quinazolin-5(3H)-ones, related tricyclic compounds, or pharmaceutically acceptable salts, is administered internally to a mammal in need thereof by a route effective to bring the compound into contact with the bronchial and tracheal tissues of the mammal. Administration can be carried out, for example, by (a) a parenteral route, such as by intravenous, intraperitoneal, or intramuscular injection; by (b) introduction into the gastrointestinal tract, for example, via oral or rectal administration in order to bring about such contact via the blood stream; or by (c) intratracheal administration, for example, by inhalation of a solution in the form of a spray, an aerosol, or as a dry powder.

The pharmaceutically effective amount of the compound, i.e., the amount sufficient to inhibit or alleviate bronchial spasm, depends on various factors. These factors include, for example, the size, type, and age of the mammal to be treated, the particular compound or pharmacologically acceptable salt employed, the route and frequency of administration, the severity of any spasm and the causative agent involved, and the time of administration. In particular cases, the dosage to be administered can be ascertained by conventional range finding techniques, for example, by observing the bronchodilating activity produced at different dosage rates. More specifically, these compounds can be administered at dosages ranging from about 0.1 to 250 mg. per kg. of mammal body weight of imidazo[2,1-b]quinazolin-5(3H)-ones, related tricyclic compounds, or pharmaceutically acceptable salts thereof. It is generally desirable to administer individual dosages at the lowest amount providing the desired protection from bronchial spasm consonant with a convenient dosing schedule. Dosage units adaptable to oral administration, such as tablets, capsules, lozenges, elixirs, syrups, and the like, are generally preferred. The active compound can also be formulated in conventional time release capsule or tablet formulations. Injectable compounds, or sprays and aerosols for inhalation, are preferred when rapid bronchodilating action is desired.

In practicing the method of the invention, the active ingredient is preferably incorporated in a composition comprising a pharmaceutical carrier from about 5 to 90 percent by weight of the imidazo[2,1-b]quinazolin-5(3H)-ones, related tricyclic compounds, or pharmaceutically acceptable salts thereof. The term "pharmaceutical carrier" refers to known pharmaceutical excipients useful in formulating pharmaceutically active compounds for internal administration to mammals, and substantially non-toxic and non-sensitizing under conditions of use. The compositions can be prepared by known techniques for the preparation of tablets, capsules, lozenges, troches, suppositories, elixirs, syrups, emulsions, dispersions, wettable and effervescent powders, sterile injectable compositions, solutions for sprays, suspensions for aerosols, and dry powders for inhalation, and can contain suitable excipients known to be useful in the preparation of the particular type of compositions desired. Suitable pharmaceutical carriers and formulation techniques are found in standard texts, such as *Remington's Pharmaceutical Sciences*, Mack Publishing Company, Easton, Pa.

In evaluating bronchodilator activity, test compounds were administered to male Hartley-Duncan guinea pigs by intraperitoneal injection. The guinea pigs were then challenged by exposure to a histamine aerosol at periods ranging from 15 minutes to 4 hours after injection of the test compound. Untreated animals collapsed when exposed to the histamine aerosol. The animals were observed and collapse times were recorded. The actual dose of test compound administered was generally 30% of the $LD_{50}$ administered intraperitoneally. When tested by the above procedure, the compounds of the present invention were found to produce a bronchodilating effect.

Some specific doses of compounds used in the testing were as follows:
(a) 2,10-dihydro-10-(dimethylamino)imidazo[2,1-b]quinazolin-5(3H)-one: 48.2 mg/kg,
(b) 2,10-dihydro-10-(1-piperidinyl)imidazo[2,1-b]quinazolin-5(3H)-one: 49.8 mg/kg, (c) 2,10-dihydro-10-(4-morpholinyl)imidazo[2,1-b]quinazolin-5(3H)-one: 49.8 mg/kg,
(d) 7-chloro-2,10-dihydro-10-(1-piperidinyl)imidazo[2,1-b]quinazolin-5(3H)-one: 20.4 mg/kg,
(e) 7-chloro-2,10-dihydro-10-(4-morpholinyl)imidazo[2,1-b]quinazolin-5(3H)-one: 18.7 mg/kg,
(f) 2,10-dihydro-7-methyl-10-(1-piperidinyl)imidazo[2,1-b]quinazolin-5(3H)-one: 70.8 mg/kg,
(g) 2,10-dihydro-7-methyl-10-(4-morpholinyl)imidazo[2,1-b]quinazolin-5(3H)-one: 27.4 mg/kg,
(h) 2,10-dihydro-10-(dimethylamino)imidazo[2,1-b]quinazolin-5(3H)-one: 63.8 mg/kg,
(i) 2,10-dihydro-10-(4-morpholinyl)imidazo[1,2-a]pyrido[2,3-d]pyrimidin-5(3H)-one: 42.2 mg/kg, and
(j) 2,10-dihydro-10-(1-piperidinyl)imidazo[1,2-a]pyrido[2,3-d]pyrimidin-5(3H)-one: 24.2 mg/kg.

The compounds of the present invention are conveniently prepared by the following reaction: A benzoyl chloride of the general formula

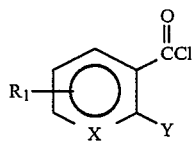

wherein
$R_1$ is a halogen, H, or $CH_3$;
Y is a halogen or $NO_2$, and when Y is a halogen, it can be F, Cl, Br, or I; and
X is —CH= or —N=,
is added to a mixture of 2-$C_{1-4}$alkylthio-2-imidazoline hydroiodide in methylene chloride. The reaction is carried out under heating. The resulting compound, an imidazoline of the general formula

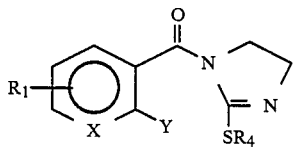

wherein $R_1$, X, and Y are defined above, and $R_4$ is $C_{1-4}$ alkyl, is reacted with a hydrazine of the general formula $H_2NNR_2R_3$ to give the compounds comprising the present invention. The reaction is carried out either neat or in an inert solvent such as diglyme, and the mixture is heated, preferably at a temperature of 160° C. or greater.

The following examples are presented to illustrate the present invention. They should not be construed as limiting it in any way.

EXAMPLE 1

1-(2-Fluorobenzoyl)-2-methylthio-2-imidazoline

A quantity of 79.1 g (1.00 mole) of pyridine was added to a slurry of 122 g (0.500 mole) of 2-imidazoline hydroiodide in 1 liter of methylene chloride. A 79.3 g (0.500 mole) quantity of o-fluorobenzoyl chloride was then added dropwise over a 15 minute period (exothermic). The mixture was heated at reflux for 15 hours, cooled, and the white precipitate was slurried with 1 liter of 1N sodium hydroxide. Insoluble white solid was collected, washed with water, and air-dried to give 63.3 g of 1-(2-fluorobenzoyl)-2-methylthio-2-imidazoline. Melting point 99°–101° C. The original precipitate was washed with water (2×200 ml), dried (sodium sulfate), and concentrated to leave an oil which crystallized on standing to give 42.6 g of additional 1-(2-fluorobenzoyl)-2-methylthio-2-imidazoline. Melting point 98°–100° C. Total yield 89%. This compound has the following formula:

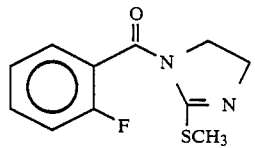

EXAMPLE 2

2,10-Dihydro-10-(4-morpholinyl)imidazo[2,1-b]quinazolin-5(3H)-one

A solution of 10.0 g (42.0 mmoles) of the product of Example 1 in 50 ml of N-aminomorpholine was heated to reflux for 10 minutes. The clear solution deposited crystals on cooling. This mixture was diluted with water (100 ml) and a white, crystalline solid was collected, washed with water, and air-dried to give 8.47 g of 2,10-dihydro-10-(4-morpholinyl)imidazo[2,1-b]quinazolin-5(3H)-one. Melting point 250°–251° C. Total yield 74%. This compound exhibits the following formula

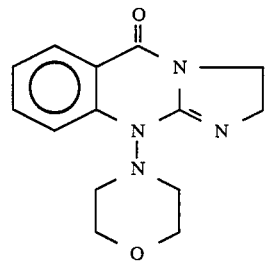

EXAMPLE 3

2,10-Dihydro-10-(1-piperidinyl)imidazo[2,1-b]quinazolin-5(3H)-one

A solution of 10.0 g (42.0 mmoles) of the product of Example 1 and 25 ml of 1-aminopiperidine in 50 ml of 2-methoxyethyl ether (diglyme) was heated at reflux for 15 hours. The solution as diluted while hot with about 5 ml of water and allowed to cool. The resulting white needles were collected, washed with ethanol, and air-dried to give 8.10 g of 2,10-dihydro-10-(1-piperidinyl)imidazo[2,1-b]quinazolin-5(3H)-one. Melting point 229°–231° C. Total yield 71%.

EXAMPLE 4

10-(Hexahydro-1H-azepin-1-yl)-2,10-dihydroimidazo[2,1-b]quinazolin-5(3H)-one

A solution of 10.0 g (42.0 mmoles) of the product of Example 1 in 50 ml of N-amino-homopiperidine was heated at reflux for 10 minutes. Upon cooling, a white, crystalline solid formed. The mixture was diluted with water (100 ml) and the solid was collected, washed with water, and air-dried to give 9.03 g of 10-(hexahydro-1H-azepin-1-yl)-2,10-dihydroimidazo[2,1-b]quinazolin-5(3H)-one. Melting point 206°–208° C. Total yield 76%.

EXAMPLE 5

2,10-Dihydro-10-(dimethylamino)imidazo[2,1-b]quinazolin-5(3H)-one

A solution of 2.40 g (10.1 mmoles) of the product of Example 1 and 3 ml of 1,1-dimethylhydrazine in 6 ml of diglyme was heated at 165° C. for 3 hours in a sealed glass tube. Upon cooling, the solution was diluted with water and the resulting solid was collected and air-dried to give 1.80 g of 2,10-dihydro-10-(dimethylamino)imidazo[2,1-b]quinazolin-5(3H)-one. Melting point 197°-198° C. Total yield 77%.

EXAMPLE 6

2,10-Dihydro-10-(1-pyrrolidinyl)imidazo[2,1-b]quinazolin-5(3H)-one

When the procedure of Example 2 is repeated using the product of Example 1 and N-aminopyrrolidine, the product obtained is 2,10-dihydro-10-(1-pyrrolidinyl)imidazo[2,1-b]quinazolin-4(3H)-one.

EXAMPLE 7

2,10-Dihydro-10-(4-methyl-1-piperazinyl)imidazo[2,1-b]quinazolin-5(3H)-one

When the procedure of Example 2 is repeated using the product of Example 1 and 1-amino-4-methylpiperazine, the product obtained is 2,10-dihydro-10-(4-methyl-1-piperazinyl)imidazo[2,1-b]quinazolin-5(3H)-one.

EXAMPLE 8

7-Chloro-2,10-dihydro-10-(4-morpholinyl)imidazo[2,1-b]quinazolin-5(3H)-one

When the procedure of Example 2 was repeated using 1-(5-chloro-2-nitrobenzoyl)-4,5-dihydro-2-(methylthio)-1H-imidazole and N-aminomorpholine, the product obtained was 7-chloro-2,10-dihydro-10-(4-morpholinyl)imidazo[2,1-b]quinazolin-5(3H)-one. Melting point 238°-239° C. Total yield 52%. This compound exhibits the following formula:

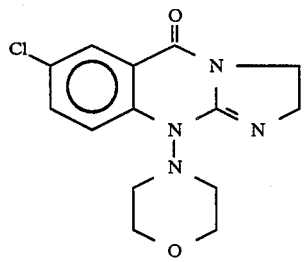

EXAMPLE 9

7-Chloro-2,10-dihydro-10-(1-piperidinyl)imidazo[2,1-b]quinazolin-5(3H)-one

When the procedure of Example 2 was repeated using 1-(5-chloro-2-nitrobenzoyl)-4,5-dihydro-2-(methylthio)-1H-imidazole and 1-aminopiperidine, the product obtained was 7-chloro-2,10-dihydro-10-(1-piperidinyl)imidazo[2,1-b]quinazolin-5(3H)-one. Melting point 192°-193° C. Total yield 16%.

EXAMPLE 10

2,10-Dihydro-7-methyl-10-(4-morpholinyl)imidazo[2,1-b]quinazolin-5(3H)-one

When the procedure of Example 2 was repeated using 4,5-dihydro-1-(5-methyl-2-nitrobenzoyl)-2-(methylthio)-1H-imidazole and N-aminomorpholine, the product obtained was 2,10-dihydro-7-methyl-10-(4-morpholinyl)imidazo[2,1-b]quinazolin-5(3H)-one. Melting point 227°-228° C. Total yield 44%. This compound exhibits the following formula:

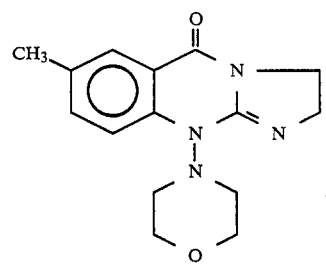

EXAMPLE 11

2,10-Dihydro-7-methyl-10-(1-piperidinyl)imidazo[2,1-b]quinazolin-5(3H)-one

When the procedure of Example 2 was repeated using 4,5-dihydro-1-(5-methyl-2-nitrobenzoyl)-2-(methylthio)-1H-imidazole and 1-aminopiperidine, the product obtained was 2,10-dihydro-7-methyl-10-(1-piperidinyl)imidazo[2,1-b]quinazolin-5(3H)-one. Melting point 197°-199° C. Total yield 16%.

EXAMPLE 12

1-(2-Chloropyridine-3-carbonyl)-2-methylthio-2-imidazoline

A mixture of 50.0 g (0.317 mole) of 2-chloropyridine-3-carboxylic acid and 120 ml of thionyl chloride was heated at reflux for 3 hours. The resulting solution was concentrated to dryness. The resulting oil was diluted twice with methylene chloride and concentrated to dryness to give 55.4 g of 2-chloropyridine-3-carbonyl chloride. Total yield 99%. This acid chloride was added to a mixture of 76.9 g (0.315 mole) of 2-methylthio-2-imidazoline hydrochloride, 1 liter of methylene chloride, and 63.7 g (0.630 mole) of triethylamine. This mixture was heated at reflux for 16 hours. The resulting solvent was removed by evaporation and the residue was stirred with water for 15 minutes. A white solid was collected by filtration and dried to give 69.2 g of 1-(2-chloropyridine-3-carbonyl)-2-methylthio-2-imidazoline; melting point 100°-102° C. Total yield 86%. This compound exhibits the following formula

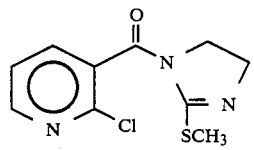

EXAMPLE 13

2,10-Dihydro-10-(4-morpholinyl)imidazo[1,2-a]pyrido[2,3-d]pyrimidin-5(3H)-one A mixture of 5.00 g (19.5 mmoles) of the product of Example 12 and 6.40 g (62.6 mmoles) of N-aminomorpholine was heated in an oil bath at 160° C. for 1 hour. The resulting mixture was cooled and partitioned between methylene chloride and water. The organic layer was dried (sodium sulfate) and concentrated. The crystalline residue was triturated with hexane. The resulting solid was collected to give 2.75 g of 2,10-dihydro-10-(4-morpholinyl)imidazo[1,2-a]pyrido[2,3-d]pyrimidin-5(3H)-one. Melting point 225°–226° C. Total yield 52%. This compound exhibits the following formula:

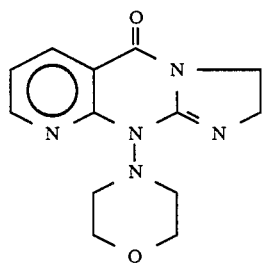

EXAMPLE 14

2,10-Dihydro-10-(1-piperidinyl)imidazo[1,2-a]pyrido[2,3-d]pyrimidin-5(3H)-one A mixture of 10.0 g (39.1 mmoles) of the product of Example 12 and 11.4 g (0.1114 mole) of 1-aminopiperidine was heated at 160° C. for 1 hour. The mixture was concentrated by Kugelrohr distillation and the residue was partitioned between methylene chloride and water. The organic layer was dried (sodium sulfate) and concentrated to a small volume. The resulting crystals were collected to give 5.74 g of 2,10-dihydro-10-(1-piperidinyl)imidazo[1,2-a]pyrido[2,3-d]pyrimidin-5(3H)-one. Melting point 206°–207° C. Total yield 54%.

EXAMPLE 15

10-(Hexahydro-1H-azepin-1-yl)-2,10-dihydroimidazo[1,2-a]pyrido[2,3-d]pyrimidin-5(3H)-one A mixture of 10.0 g (39.1 mmoles) of the product of Example 12 and 12.5 g (0.109 mole) of N-aminohomopiperidine was heated at 160° C. for 1 hour. Excess N-aminohomopiperidine was removed by Kugelrohr distillation and the residue was partitioned between methylene chloride and water. The organic layer was dried (sodium sulfate) and concentrated leaving 7.40 g of 10-(hexahydro-1H-azepin-1yl)-2,10-dihydroimidazo[1,2-a]pyrido[2,3-d]pyrimidin-5(3H)-one; melting point 217°–219° C. Total yield 66%.

We claim:

1. A compound of the formula:

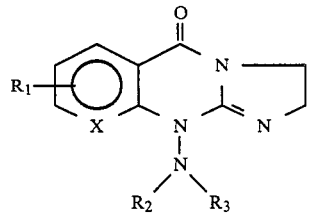

wherein $R_1$ is H, halogen, or $CH_3$;

$NR_2R_3$ is di(lower alkyl) amino, 1-pyrrolidinyl, 1-piperidinyl, 1-homopiperidinyl, 4-methyl-1-piperazinyl, or 4-morpholinyl; and X is —CH= or —N=.

2. A compound according to claim 1 having the formula:

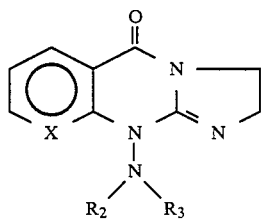

wherein $NR_2R_3$ is di(lower alkyl) amino, 1-pyrrolidinyl, 1-piperidinyl, 1-homopiperidinyl, 4-methyl-1-piperazinyl, or 4-morpholinyl;

X is —C= or —N=.

3. A compound according to claim 1 having the formula:

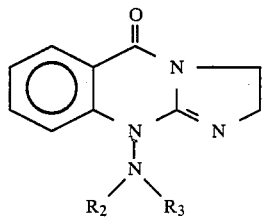

wherein $NR_2R_3$ is di(lower alkyl) amino, 1-pyrrolidinyl, 1-piperidinyl, 1-homopiperidinyl, 4-methyl-1-piperazinyl, or 4-morpholinyl.

4. A compound according to claim 1 having the formula:

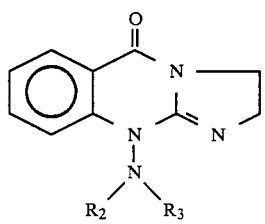

wherein $NR_2R_3$ is 1-pyrrolidinyl, 1-piperidinyl, 1-homopiperidinyl, 4-methyl-1-piperazinyl, or 4-morpholinyl.

5. A compound of claim 1 which is 2,10-dihydro-10-(4-morpholinyl)imidazo[2,1-b]quinazolin-5(3H)-one.

6. A compound of claim 1 which is 2,10-dihydro-10-(1-pyrrolidinyl)imidazo[2,1-b]quinazolin-5(3H)-one.

7. A compound of claim 1 which is 2,10-dihydro-10-(1-piperidinyl)imidazo[2,1-b]quinazolin-5(3H)-one.

8. A compound of claim 1 which is 10-(hexahydro-1H-azepin-1-yl)-2,10-dihydroimidazo[2,1-b]quinazolin-5(3H)-one.

9. A compound of claim 1 which is 2,10-dihydro-10-(dimethylamino)imidazo[2,1-b]quinazolin-5(3H)-one.

10. A compound of claim 1 which is 2,10-dihydro-10-(4-morpholinyl)imidazo[1,2-a]pyrido[2,3-d]pyrimidin-5(3H)-one.

11. A compound of claim 1 which is 2,10-dihydro-10-(1-pyrrolidinyl)imidazo[1,2-a]pyrido[2,3-d]pyrimidin-5(3H)-one.

12. A compound of claim 1 which is 2,10-dihydro-10-(1-piperidinyl)imidazo[1,2-a]pyrido[2,3-d]pyrimidin-5(3H)-one.

13. A compound of claim 1 which is 10-(hexahydro-1H-azepin-1-yl)-2,10-dihydroimidazo[1,2-a]pyrido[2,3-d]pyrimidin-5(3H)-one.

14. A method of producing bronchodilation which comprises administering a pharmaceutically effective amount of a compound of claim 1 to a mammal in need thereof.

* * * * *